United States Patent

Komori et al.

(10) Patent No.: US 6,514,720 B2
(45) Date of Patent: *Feb. 4, 2003

(54) METHOD OF MEASURING SUBSTANCE IN SAMPLE USING A REDOX REACTION

(75) Inventors: Tsuguki Komori, Kyoto (JP); Satoshi Yonehara, Kyoto (JP)

(73) Assignee: Kyoto Daiichi Kagaku Co., Ltd., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/947,900

(22) Filed: Sep. 5, 2001

(65) Prior Publication Data

US 2002/0025546 A1 Feb. 28, 2002

Related U.S. Application Data

(63) Continuation of application No. 09/440,241, filed on Nov. 15, 1999, now Pat. No. 6,352,835.

(51) Int. Cl.$^7$ .............................. C12Q 1/26; C12Q 1/00; C12Q 1/54; C12Q 1/37
(52) U.S. Cl. ............................. 435/25; 435/4; 435/14; 435/23; 436/66; 548/250
(58) Field of Search ................................. 435/25, 4, 14, 435/23, 24; 436/66; 548/250

(56) References Cited

U.S. PATENT DOCUMENTS

| | | | |
|---|---|---|---|
| 4,310,626 A | 1/1982 | Burhkardt et al. ............ 435/25 |
| 4,587,220 A | 5/1986 | Mayambala-Mwanika et al. ............................ 435/25 |
| 4,743,559 A | 5/1988 | Koever et al. ................. 435/25 |
| 4,755,472 A | 7/1988 | Ismail et al. ................... 435/25 |
| 4,954,451 A | 9/1990 | Albarella et al. .............. 435/25 |
| 4,957,872 A | 9/1990 | Koever et al. ................. 435/25 |
| 5,013,647 A | 5/1991 | Town et al. ................... 435/25 |
| 5,116,762 A | 5/1992 | Vogt et al. ..................... 435/25 |
| 5,196,314 A | 3/1993 | Town et al. ................... 435/25 |
| 6,352,835 B1 * | 3/2002 | Komori et al. ................ 435/25 |

FOREIGN PATENT DOCUMENTS

| | | |
|---|---|---|
| EP | 0 239 931 A2 | 10/1987 |
| EP | 0 463 171 A1 | 1/1992 |
| EP | 0 698 413 A2 | 2/1996 |
| JP | 57-161650 | 10/1982 |
| WO | 90/12113 | 4/1990 |

* cited by examiner

*Primary Examiner*—Louise N. Leary
(74) *Attorney, Agent, or Firm*—Merchant & Gould P.C.

(57) ABSTRACT

A highly reliable method of measuring an analyte in a sample using a redox reaction. In this method, a tetrazolium compound is added to a sample prior to the redox reaction so as to eliminate the influence of any reducing substance in the sample, then a reducing substance or an oxidizing substance derived from the analyte is formed, the quantity of the formed substance derived from the analyte is measured by the redox reaction, and the quantity of the analyte is determined from the quantity of the formed substance derived from the analyte. As the tetrazolium compound, for example, 2-(4-iodophenyl)-3-(2,4-dinitrophenyl)-5-(2,4-disulfophenyl)-2H-tetrazolium salt can be used.

16 Claims, No Drawings

METHOD OF MEASURING SUBSTANCE IN SAMPLE USING A REDOX REACTION

This is a continuation of application Ser. No. 09/440,241, filed Nov. 15, 1999, now U.S. Pat. No. 6,352,835.

FIELD OF THE INVENTION

The present invention relates to a method of measuring an analyte in a sample using a redox reaction.

BACKGROUND OF THE INVENTION

Traditionally, measurement of the quantity of an analyte in a sample using a redox reaction has been utilized in a wide range of applications. For example, such a measurement has been utilized for measuring glycated proteins in applications such as biocheminical analyses, clinical tests, and the like.

For instance, glycated proteins in blood, particularly glycated hemoglobin (HbAlc) in erythrocytes, are significant indicators in the diagnosis and therapy of diabetes, because they reflect the patient's past history of blood sugar value. Glycated proteins in erythrocytes are measured using a redox reaction, for example, as follows:

First, erythrocytes are hemolyzed to prepare a sample. The hemolyzed sample is treated with a suitable protease or the like, and then treated with fructosyl amino acid oxidase (hereinafter referred to as FAOD) so as to form hydrogen peroxide. The quantity of the hydrogen peroxide formed corresponds to the quantity of glyated proteins in erythrocytes. Then, a peroxidase (hereinafter referred to as POD) and a reducing agent are added to the sample, so that a redox reaction occurs between the hydrogen peroxide and the reducing agent with the POD as a catalyst. At this time, when a reducing agent that develops color when it is oxidized is used, the quantity of the hydrogen peroxide can be determined by measuring the color. As a result, the quantity of the glycated proteins in erythrocytes can be determined.

However, various kinds of reducing substances, such as L-ascorbic acid (AsA) and bilirubin, are usually present in blood. Moreover, various types of reducing substances such as glutathione (GSH) and the like are present in erythrocytes. These reducing substances may reduce the hydrogen peroxide, or may inhibit the redox reaction, or may reduce the reducing agent after it develops color, so as to cause degradation of the color. Therefore, there has been a problem that it is difficult to determine the quantity of the glycated proteins in erythrocytes accurately.

There has been also another problem, that precision of the measurement may deteriorate because the concentrations of the reducing substances contained in samples are not constant.

In order to avoid these problems, for example, various types of oxidizing agents have been added to samples. For example, Publication of Unexamined Japanese Patent Application No. Sho 56-151358 discloses a method of using halogen oxides, such as iodic acid or periodic acid, as oxidizing agents. Publications of Unexamined Japanese Patent Applications No. Sho 57-13357, No. Sho 57-161650, No. Sho 59-193354, No. Sho 62-169053, and No. Hei 3-30697 also disclose methods of using complexes of metals such as cobalt, iron, cerium, etc. as oxidizing agents.

However, the effect of the reducing substances on the measurements can not be avoided sufficiently even with the use of these oxidizing agents. In particular, these oxidizing agents performed poorly when the analyte was a component in erythrocytes.

SUMMARY OF THE INVENTION

Accordingly, it is an object of the present invention to provide a highly reliable method of measuring an analyte in a sample using a redox reaction.

In order to accomplish this object, the present invention provides a method of measuring an analyte in a sample using a redox reaction, comprising: adding a tetrazolium compound prior to the redox reaction to a sample so as to eliminate the influence of any reducing substance contained in the sample; then forming a reducing substance or an oxidizing substance derived from the analyte; measuring the quantity of the formed substance derived from the analyte by the redox reaction; and determining the quantity of the analyte from the quantity of the formed substance. The tetrazolium compound herein refers to a compound having a tetrazole ring.

As a result of extensive studies. the inventors found that the cause of the problems in the conventional methods was not that the influence of the low molecular weight reducing substances such as the above-mentioned GSH and AsA were not eliminated, but that the influence of high molecular weight reducing substances such as proteins or the like were not eliminated. The inventors also found that, not only the influence of the low molecular weight reducing substances, but also influence of other reducing substances can be eliminated by the use of the tetrazolium compound, and thus have reached the method of the present invention. According to the method of the present invention, the quantity of the analyte can be determined with greater reliability. Thus, it is used suitably for various kinds of tests. e.g. in clinical medicine.

In the method of the present invention, it is preferable that the tetrazolium compound has cyclic substituted groups in at least two positions of its tetrazole ring. More preferably, it has cyclic substituted groups at three positions thereof.

When the tetrazolium compound has cyclic substituted groups in at least two positions of its tetrazole ring as mentioned above, it is preferable that the substituted groups are at positions 2 and 3 thereof. Moreover, when the tetrazolium compound has cyclic substituted groups at three positions of its tetrazole ring, it is preferable that the substituted groups are at positions 2, 3, and 5 thereof.

In the method of the present invention, it is preferable that at least two of the cyclic substituted groups have benzene rings. Moreover, cyclic substituted groups other than those having benzene rings include, for example, substituted groups containing S or O in their ring skeletons and having resonance structures, such as thienyl and thiazolyl groups, and the like.

In the method of the present invention, it is preferable that the tetrazolium compound has cyclic substituted groups in at least three positions of its tetrazole ring, and that at least two of the cyclic substituted groups have benzene rings.

In the method of the present invention, it is preferable that at least one of the cyclic substituted groups has functional groups. It is more preferable that the number of the functional groups is large.

Preferable examples of the functional groups are electron attractive functional groups, e.g. halogen atoms or ether, ester, carboxyl, acyl, nitroso, nitro, hydroxyl or sulfo groups, and the like. Examples other than these functional groups are groups containing oxygen, such as hydroperoxy, oxy, epoxy, epidioxy, and oxo groups, and groups containing sulfur, such as mercapto, alkylthio, methylthiomethyl, thioxo, sulfino, benzenesulfonyl, phenylsulfonyl, p-toluenesulfonyl, p-tolylsulfonyl, tosyl, sulfamoyl, and isothiocyanato groups. Among the electron attractive functional groups, preferable are halogen atoms and nitro, sulfo, carboxyl, hydroxyl, methoxy, and ethoxy groups. Furthermore, examples other than the above-mentioned electron attractive functional groups include unsaturated hydrocarbon groups, such as phenyl group ($C_6H_5$—), styryl group ($C_6H_5CH=CH$—), and the like. Moreover, the functional groups may be ionized by dissociation.

In the method of the present invention, it is preferable that the tetrazolium compound has benzene rings at positions 2 and 3 of its tetrazole ring, and that at least one of the benzene rings has at least one functional group selected from the group consisting of halogen atoms and carboxyl, nitro, hydroxyl, sulfo, methoxy, and ethoxy groups. Moreover, both of the benzene rings may have such functional groups. The benzene ring may have the functional groups at any position (i.e. ortho-, meta-, or para-). Furthermore, the number of the functional groups is not particularly limited, and the benzene ring may have either the same or different functional groups.

In the method of the present invention, examples of the tetrazolium compound include those having substituted groups with benzene rings at positions 2, 3 and 5 of their tetrazole rings, e.g. 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl)-2H-tetrazolium salt, 2-(2-methoxy-4-nitrophenyl)-3-(4-nitrophenyl)-5-(2,4-disulfophenyl)-2H-tetrazolium salt, 2-(4-iodophenyl)-3-(4-nitrophenyl)-5-phenyl-2H-tetrazolium salt, 3,3'-(1,1'-biphenyl-4,4'-diyl)-bis(2,5-diphenyl)-2H-tetrazolium salt, 3,3'-[3,3'-dimethoxy-(1,1'-biphenyl)-4,4'-diyl]-bis[2-(4-nitropenyl)-5-phenyl-2H-tetrazolium salt], 2,3-diphenyl-5-(4-chlorophenyl)tetrazolium salt, 2,5-diphenyl-3-(p-diphenyl)tetrazolium salt, 2,3-diphenyl-5-(p-diphenyl)tetrazolium salt, 2,5-diphenyl-3-(4-styrylphenyl)tetrazolium salt, 2,5-diphenyl-3-(m-tolyl)tetrazolium salt, and 2,5-diphenyl-3-(p-tolyl)tetrazolium salt, and the like.

Furthermore, the tetrazolium compound is not limited to the above-mentioned compounds, and other compounds having cyclic substituted groups with benzene rings at two positions of their tetrazole rings and other cyclic substituted group at one position thereof also can be used. Examples of such compounds include 2,3-diphenyl-5-(2-thienyl)tetrazolium salt, 2-benzothiazoyl-3-(4carboxy-2-methoxyphenyl)-5-[4-(2-sulfoethyl carbamoyl)phenyl]-2H-tetrazolium salt, 2,2'-dibenzothiazolyl-5,5'-bis[4-di(2-sulfoethyl)carbamoylphenyl]-3,3'-(3,3'-dimethoxy-4,4'-biphenylene)ditetrazolium salt, 3-(4,5-dimethyl-2-thiazoyl)-2,5-diphenyl-2H-tetrazolium salt, and the like.

Furthermore, tetrazolium compounds having substituted groups with benzene rings at two positions of their tetrazole rings and a non-cyclic substituted group at one position thereof also can be used. Examples of such compounds include 2,3-diphenyl-5-cyanotetrazolium salt, 2,3-diphenyl-5-carboxytetrazolium salt, 2,3-diphenyl-5-methyltetrazolium salt, and 2,3-diphenyl-5-ethyltetrazolium salt, and the like.

Among the above-mentioned tetrazolium compounds, preferable are those having three cyclic substituted groups as mentioned above, and more preferable are those having three cyclic substituted groups with benzene rings and having many electron attractive functional groups. Particularly preferable is 2-(4-iodophenyl)-3-(2,4-dinitrophenyl)-5-(2,4-disulfophenyl)-2H-tetrazolium salt. Moreover, these tetrazolium compounds may be, for example, in the forms of salts, or may be in ionized forms.

In the method of the present invention, the amount of the tetrazolium compound added is not particularly limited, and it can be determined as appropriate depending on the type of the sample and the amount of the reducing substance. Specifically, it is preferable that the tetrazolium compound is added so that its concentration falls in the range of 0.001 to 100 $\mu$mol, more preferably from 0.005 to 10 $\mu$mol, particularly preferably from 0.01 to 1 $\mu$mol per 1 $\mu$l of the sample.

In the method of the present invention, when the sample is whole blood, it is preferable that the tetrazolium compound is added in an amount such that its concentration falls in the range of 0.001 to 10 $\mu$mol per 1 $\mu$l of whole blood. More preferably it is in the range of 0.005 to 5 $\mu$mol, particularly preferably from 0.01 to 1 $\mu$mol per 1 $\mu$l of whole blood. Specifically, when the tetrazolium compound is 2-(4-iodophenyl)-3-(2,4-dinitrophenyl)-5-(2,4-disulfophenyl)-2H-tetrazolium salt, it is preferably added in an amount such that its concentration falls in the range of 0.001 to 0.4 $\mu$mol per 1 $\mu$l of whole blood. More preferably it is in the range of 0.005 to 0.1 $\mu$mol, particularly preferably from 0.01 to 0.07 $\mu$mol per 1 $\mu$l of whole blood.

In the method of the present invention, it is preferable that the oxidizing substance derived from the analyte is hydrogen peroxide, and that the quantity of the hydrogen peroxide is measured by the redox reaction.

It is preferable that the quantity of the hydrogen peroxide is measured using a substrate that develops color by oxidation with an oxidizing enzyme (hereinafter referred to as a color-developing substrate).

Although not particularly limiting, it is preferable that, for example, N-(carboxymethylaminocarbonyl)-4,4'-bis (dimethylamino)diphenylamine sodium is used as the color-developing substrate, because this can be detected with high sensitivity. Furthermore, it is preferable that the oxidizing enzyme is a peroxidase.

In the method of the present invention, the type of the sample is not particularly limited. The method also can be applied to samples other than whole blood, plasma, serum, and blood cells, e.g. biological samples such as urine and spinal fluid, drinks such as juices, foods such as soy sauce and Worcester sauce.

In the method of the present invention, the analyte may be, for example, components in whole blood, components in erythrocytes, components in plasma, components in serum, components in urine, components in spinal fluid, and the like, and it is preferably a component in erythrocytes. The component in erythrocytes may be, for example, glycated protein such as glycated hemoglobin and glycated albumin, glycated peptide, glycated amino acid, glucose, uric acid, cholesterol, creatinine, sarcosine, glycerol, and the like, particularly glycated protein. For example, when a component in erythrocytes is to be measured, whole blood itself may be hemolyzed to prepare a sample, or erythrocytes are separated from whole blood and hemolyzed to prepare a sample.

In the method of the present invention, it is preferable that hydrogen peroxide is formed by decomposing sugar portions of glycated proteins by oxidation with FAOD. Furthermore, it is preferable that glycated peptides and glycated amino acids also are subjected to the action of FAOD. Moreover, it is preferable that glycated proteins and glycated peptides are treated with a protease before its treatment with FAOD as necessary.

It is preferable that the FAOD catalyzes a reaction represented by a formula (1) below.

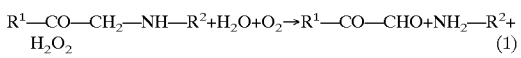  (1)

In the formula (1) above, $R^1$ denotes a hydroxyl group or a residue derived from the sugar before glycation (i.e. a sugar residue). The sugar residue ($R^1$) is an aldose residue when the sugar before glycation is an aldose, and is a ketose residue when the sugar before glycation is a ketose. For example, when the sugar before glycation is glucose, it takes a fructose structure after glycation by an Amadori rearrangement. In this case, the sugar residue ($R^1$) becomes a glucose residue (an aldose residue). The sugar residue ($R^1$) can be represented, for example, by

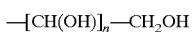

where n is an integer of 0 to 6.

In the formula (1) above, although the type of $R^2$ is not particularly limited, when it is a glycated amino acid, glycated peptide, or glycated protein, there is a difference between the case of α-amino group being glycated and the case of other amino group being glycated.

In the formula (1) above, when an α-amino group is glycated, $R^2$ is an amino acid residue or a peptide residue represented by a formula (2) below.

$$—CHR^1—CO—R^4$$  (2)

In the formula (2) above, $R^3$ indicates an amino acid side chain group. Furthermore, $R^4$ denotes a hydroxyl group, an amino acid residue, or a peptide residue, and can be represented, for example, by a formula (3) below. In the formula (3) below, n is an integer of not less than zero, and $R^3$ denotes an amino acid side chain group as in the above.

$$—(NH—CHR^3—CO)_n—OH$$  (3)

Furthermore, in the formula (1) above, when an amino group other than α-amino group is glycated (i.e. when an amino acid side chain group is glycated), $R^2$ can be represented by a formula (4) below.

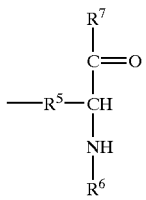  (4)

In the formula (4) above, $R^5$ indicates the portion of the amino acid side chain group other than the glycated amino group. For example, when the glycated amino acid is lysine, $R^5$ is $$—CH_2—CH_2—CH_2—CH_2—.$$

For another example, when the glycated amino acid is arginine, $R^5$ is $$—CH_2—CH_2—CH_2—NH—CH(NH_2)—.$$

Furthermore, in the formula (4) above, $R^6$ denotes hydrogen, an amino acid residue, or a peptide residue. It can be represented, for example, by a formula (5) below.

Moreover, in the formula (5) below, n is an integer of not less than zero, and $R^3$ denotes an amino acid side chain group as in the above.

$$—(CO—CHR^3—NH)_n—H$$  (5)

Furthermore, in the formula (4) above, $R^7$ denotes hydroxyl group, an amino acid residue, or a peptide residue. It can be represented, for example, by a formula (6) below. Moreover, in the formula (6) below, n is an integer of not less than zero, and $R^3$ denotes an amino acid side chain group as in the above.

$$—(NH—CHR^3—CO)_n—OH$$  (6)

In the method of the present invention, although it is not particularly limiting, the molecular weight of the reducing substance in the sample is, for example, at least 10,000, preferably from 10,000 to 3,000,000, more preferably from 10,000 to 300,000. particularly preferably from 30,000 to 100,000.

Furthermore, it is preferable that the reducing substance in the sample is a protein. The molecular weight of the protein is, for example, at least 3,000, preferably from 3,000 to 3,000,000, more preferably from 10,000 to 300,000, particularly preferably from 30,000 to 100,000. Examples of such a reducing substance include hemoglobin, globin, globulin, albumin, and the like, preferably hemoglobin.

DETAILED DESCRIPTION OF THE INVENTION

The methods of the present invention are described in detail below with reference to the following examples, in which glycated proteins in blood cells are measured.

First, whole blood itself is hemolyzed, or a blood cell fraction is separated from whole blood by a conventional method such as centrifugation and hemolyzed, so as to prepare a hemolyzed sample. The method of the hemolysis is not particularly limited, and for example, methods of using a surfactant, ultrasonic waves, osmotic pressure difference, etc. can be employed. Among these methods, it is preferable to employ a method using a surfactant because of its simplicity in operation, etc.

As the surfactant, for example, non-ionic surfactants such as polyoxyethylene-p-t-octylphenyl ether (e.g. Triton series surfactants), polyoxyethylene sorbitan alkyl ester (e.g. Tween series surfactants), polyoxyethylene alkyl ether (e.g. Brij series surfactants), and the like can be used. Specific examples are Triton X-100, Tween-20, Brij 35, and the like. The conditions of the treatment with the surfactant is usually as follows: when the concentration of blood cells in the treating solution is from 1 to 10% by volume, the surfactant is added so that its concentration in the treating solution falls in the range of 0.01 to 5% by weight, and stirred at room temperature for about several seconds (about 5 seconds) to 10 minutes.

Next, the tetrazolium compound having a tetrazole ring is added to the hemolyzed sample to carry out pretreatment of the sample.

For example, when the concentration of blood cells in the pretreatment solution is from 1 to 10% by volume, it is preferable that the tetrazolium compound is added so that its concentration falls in the range of 0.02 to 2000 mmol/liter, more preferably from 0.1 to 1000 mmol/liter, particularly preferably from 0.4 to 200 mmol/liter. Specifically, when the tetrazolium compound is 2-(4-iodophenyl)-3-(2,4-dinitrophenyl)-5-(2,4-disulfophenyl)-2H-tetrazolium salt, preferably it is added so that its concentration falls in the range of 0.02 to 80 mmol/liter, more preferably from of 0.1 to 20 mmol/liter, particularly preferably from 0.2 to 15 mmol/liter.

The pretreatment is usually carried out in a buffer. For example, CHES, CAPSO, CAPS, phosphate, Tris, EPPS, HEPES buffers, and the like, can be used. The pH of the buffer is, for example, in the range of 6 to 13, preferably from 8 to 12, more preferably from 9 to 11. Moreover, the final concentration of the buffer in the pretreatment solution is, for example, from 1 to 400 mmol/liter, preferably from 10 to 200 mmol/liter.

The conditions of the pretreatment are not particularly limited, but it is usually carried out at a temperature of 10 to 37° C. for a period of 10 seconds to 60 minutes.

Although the tetrazolium compound may be used simply as it is, it is preferably used as a solution in which the tetrazolium compound is dissolved in a solvent, in terms of simplicity in operation and efficiency of the treatment. The concentration of the solution can be determined as appropriate depending on the type of the tetrazolium compound (e.g. molecular weight, etc.), etc. For example, the concentration is in the range of 0.01 to 120 mmol/liter, preferably from 0.1 to 50 mmol/liter, more preferably from 0.2 to 20 mmol/liter. As the solvent, for example, distilled water, physiological saline, buffers, or the like can be used. As the buffers, for example, the same buffers as mentioned above can be employed. Moreover, the tetrazolium compound may be used either alone or in combination of two or more types.

Next, the pretreated hemolyzed sample is treated with a protease. This treatment is performed so that the FAOD used in the subsequent treatment may act on the analyte more easily.

The type of the protease is not particularly limited, and for example, protease K, subtilisin, trypsin, aminopeptidase, and the like can be used. The protease treatment is usually carried out in a buffer, and the conditions of the treatment are determined as appropriate depending on the type of the protease used, the type and the concentration of the glycated proteins as the analytes, etc.

Specifically, when the pretreated hemolyzed sample is treated using protease K, the protease treatment is usually carried out under the conditions as follows: a concentration of the protease in the reaction solution of 10 to 30,000 mg/liter; a concentration of blood cells in the reaction solution of 0.05 to 15% by volume; a reaction temperature of 15 to 37° C.; a reaction period of 1 minute to 24 hours; and a pH of 6 to 12. Moreover, the type of the buffer is not particularly limited, and for example, Tris-HCl buffer, EPPS buffer, PIPES buffer, and the like can be used.

Next, a decomposed material obtained by the protease treatment is further treated with the FAOD. The reaction shown by the formula (1) above is catalyzed by this FAOD treatment.

It is preferable that the FAOD treatment is carried out in a buffer as in the above protease treatment. The conditions of the FAOD treatment are determined as appropriate depending on the type of the FAOD used, the type and the concentration of the glycated proteins as the analytes, etc.

Specifically, the conditions are as follows: a concentration of the FAOD in the reaction solution of 5.0 to 50,000 U/iter; a concentration of blood cells in the reaction solution of 0.01 to 1% by volume; a reaction temperature of 15 to 37° C.; a reaction period of 1 to 60 minutes; and a pH of 6 to 9. Moreover, the type of the buffer is not particularly limited, and for example, the same buffers as in the protease treatment can be used.

Next, the hydrogen peroxide formed in the FAOD treatment is measured by a redox reaction using POD and the color-developing substrate.

Examples of the color-developing substrate include N-(carboxymethylaminocarbonyl)-4,4'-bis(dimethylamino) diphenylamine sodium, orthophenylenediamine (OPD), and a substrate in which trinder's reagent and 4-aminoantipyrine are combined, and the like. Examples of the trinder's reagent are phenol, phenol derivatives, aniline derivatives, naphthol, naphthol derivatives, naphthylamine, naphthylamine derivatives, and the like. Moreover, in place of the aminoantipyrine, aminoantipyrine derivatives, vanillin diamine sulfonic acid, methylbenzothiazolinonehydrazone (MBTH), sulfonated methylbenzothiazolinonehydrazone (SMBTH), and the like, also can be used. Among these color-developing substrates, particularly preferable is N-(carboxymethylaminocarbonyl)-4,4'-bis(dimethylamino) diphenylamine sodium, as mentioned above.

The redox reaction is usually carried out in a buffer. The conditions of the reaction are determined as appropriated depending of the concentration of the hydrogen peroxide formed, etc. The conditions are usually as follows: a concentration of the POD in the reaction solution of 10 to 100,000 IU/liter; a concentration of the color-developing substrate of 0.005 to 30 mmol/liter; a reaction temperature of 15 to 37° C.; a reaction period of 0.1 to 30 minutes; and a pH of 5 to 9. Moreover, the type of the buffer is not particularly limited, and for example, the same buffers as in the protease treatment and the FAOD treatment can be used.

In the redox reaction, for example. when the color-developing substrate is used, the quantity of the hydrogen peroxide can be determined by measuring the degree of the color developed (i.e. absorbance) in the reaction solution with a spectrophotometer. Then, for example, the quantity of the glycated proteins in the sample can be determined using the concentration of the hydrogen peroxide and a calibration curve.

Moreover, the quantity of the hydrogen peroxide also can be determined by a method other than the above-mentioned enzymatic method using POD, for example, by an electrical method.

In this method, the pretreatment step with a tetrazolium compound is not particularly limited as long as it is carried out before the redox reaction actually occurs as described above. However, because the hydrogen peroxide is formed after the FAOD treatment, it is preferable that the pretreatment step is performed before the FAOD treatment. Moreover, although each of the treating steps may be carried out separately as described above, some of the treating steps also may be performed simultaneously, for example, in the combinations as follows:

1: hemolysis treatment+pretreatment
2: hemolysis treatment+pretreatment+protease treatment
3: protease treatment+FAOD treatment
4: FAOD treatment+POD redox treatment
5: protease treatment+FAOD treatment+POD redox treatment Furthermore, the order of adding the FAOD, the POD, and the color-developing substrate also is not particularly limited.

Thus, by contacting a sample with a tetrazolium compound, not only the influence of low molecular weight reducing substances such as GSH, AsA, dithiothreitol, cysteinie, N-acetyl-cysteine, and the like, but also the influence of, for example, proteins or reducing substances having molecular weights in the above-mentioned range can be avoided.

Furthermore, in the pretreatment step with the tetrazolium compound in the method of the present invention, for example, an oxidizing agent other than the tetrazolium compound also may be used in combination. As such an oxidizing agent, for example, a halogen oxide such as sodium iodoacetate, iodic acid, periodic acid, or the like, or EDTA-Fe, ascorbic acid oxidase, bilirubin oxidase, or the like can be used. The amount of such an oxidizing agent added is, for example, in the range of 0.001 to 0.1 mg per 1 $\mu$l of the sample.

In the method of the present invention, the analyte is not particularly limited, as long as a redox reaction is utilized. Examples of the analyte other than the above-mentioned glycated proteins include glycated peptides, glycated amino acids, glucose, cholesterol, uric acid, creatinine, sarcosine, glycerol, and the like, as mentioned above.

When the quantity of each of the above-mentioned examples of the analyte is measured by forming hydrogen peroxide, the hydrogen peroxide is formed, for example by action of: a glucose oxidase on the glucose: a cholesterol oxidase on the cholesterol; an uricase on the uric acid; a sarcosine oxidase on the creatinine; a sarcosine oxidase on the sarcosine; or a glycerol oxidase on the glycerol; respectively. The quantity of the hydrogen peroxide can be measured in the same way as above. Moreover, glycated peptides and glycated amino acids can be measured, for example, in the same way as in the measurement of the glycated proteins above.

Furthermore, after the treatment of the reducing substances in a sample with the tetrazolium compound, when the quantity of the analyte is determined by forming a reducing substance derived from the analyte, measuring the quantity of the reducing substance by a redox reaction, and determining the quantity of the analyte from the quantity of the reducing substance, the measurement can be carried out, for example, as follows:

When the analyte is glucose, for example, a reducing substance such as NADH or NADPH is formed using glucose dehydrogenase in the presence of NAD, NADP, or the like. Then, the NADH or NADPH as a reducing substance derived from the analyte is measured by a redox reaction, using, for example, diaphorase and a substrate that develops color by reduction. Then, as mentioned above, the quantity of the analyte in the sample can be determined, for example, using the concentration of the reducing substance derived from the analyte and a calibration curve or the like. Furthermore, for example, cholesterol dehydrogenase can be used when the analyte is cholesterol, and sarcosine dehydrogenase can be used when the analyte is sarcosine.

As the substrate that develops color by reduction, although not particularly limited, for example, a color-developing tetrazolium compound added to eliminate the influences of the reducing substances in the sample may be employed. Furthermore, a different type of a color-developing tetrazolium compound other than the one used in the pretreatment of the sample also may be employed depending on each wavelength of the measurement. Other than the above-mentioned color-developing tetrazolium compounds, for example, 2,6-dichlorophenolindophenol and the like also can be employed. Moreover, in order to obtain measured values with more excellent reliability, for example, it is preferable to measure an absorbance in advance before measuring the reducing substance derived from the analyte.

Moreover, when a sample is thus treated with the tetrazolium compound, not only the influence of the above-mentioned low molecular weight reducing substances, but also the influence of the above-mentioned high molecular weight reducing substances such as proteins can be avoided. Therefore, when there is an influence of a reducing substance having a molecular weight of at least 10,000 or a reducing substance as a protein, the method can be applied not only to the whole blood sample, but also to the above-mentioned various kinds of samples. Moreover, when a sample other than whole blood is used, the measurement can be carried out in the same manner using the same reagents, except that the sample is different.

In the following, the present invention is described with reference to the following examples and comparative examples.

EXAMPLE 1

Comparative Example 1

In Example 1, a sample was pretreated with a tetrazolium compound so as to eliminate the influence of any reducing substance in the sample. The following shows the reagents and methods used in Example 1.

Surfactant Solution

Polyoxyethylene(10)-p-t-octylphenyl ether (hereinafter referred to as Triton X-100) was mixed with purified water so that its concentration became 0.1% by volume.

2-(4-idophenyl)-3-(2,4-dinitrophenyl)-5-(2,4-disulfophenyl)-2H-tetrazolium, monosodium salt (WST-3, produced by DOJINDO LABORATORIES) was dissolved in purified water so that its concentration became 1 mmol/liter.

Fructosyl Valine Solution

Fructosyl valine (hereinafter referred to as FV) was produced in accordance with the method disclosed in Publication of Unexamined Japanese Patent Application No. Hei 2-69644 (hereinafter the same). The FV was added to 0.5 mol/liter Tris-HCl buffer (pH 8.0) so that its concentration became 50 $\mu$mol/liter.

| Redox reaction solution A | |
|---|---|
| FAOD (produced by Asahi Chemical Industry, Co., Ltd.; hereinafter the same) | 28.6 KU/liter |
| POD (produced by TOYOBO CO., LTD; hereinafter the same) | 14.3 KU/liter |
| DA-64 (produced by Wako Pure Chemical Industries, LTD.; hereinafter the same) | 28.6 $\mu$mol/liter |
| Distilled water | remaining portion |

Whole blood from a healthy adult was subjected to centrifugation (1630 G, for 10 minutes) so as to collect blood cells. Then, the blood cells were diluted 20-fold (by volume) with the Triton X-100 solution, and hemolyzed to prepare a hemolyzed sample.

50 $\mu$l of 0.5 mol/liter CHES buffer (pH 9.0) was added to 50 $\mu$l of the sample, and then 100 $\mu$l of the WST-3 solution was added thereto and stirred. Thereafter, it was treated at 37° C. for 10 minutes. After this treatment, 400 $\mu$l of the FV solution was added to the sample, and then 1,400 $\mu$l of the redox solution A was added thereto so as to start a reaction. Then, absorbance of the reaction solution was measured at 726 nm.

As a control, measurement was called out in the same manner as in the above except that distilled water was used in place of the hemolyzed sample. As Comparative Example 1, the same measurement as in Example 1 was carried out except that distilled water was used in place of the WST-3 solution.

Then, the measured values were substituted in an equation (1) below, and a relative value (%) was determined by setting the absorbance of the control as 100%. These results are shown in Table 1 below.

$$\text{Relative value (\%)} = (X_1 - X_0 / Y_1 - Y_0) \times 100 \quad \text{(Eq. 1)}$$

$X_1$: absorbance after 5 minutes
$X_0$: absorbance at the start of the reaction
$Y_1$: absorbance after 5 minutes in control
$Y_0$: absorbance at the start of the reaction in control

TABLE 1

|  | Relative value (%) |
|---|---|
| Example 1 | 83 |
| Comparative Example 1 | 34 |
| Control | 100 |

Thus, by treating a hemolyzed sample of blood cells with a tetrazolium compound, the influence of the reducing substance in the sample was eliminated, so that reliability of the measurement was improved.

Comparative Examples 2 and 3

According to the same procedures as in Example 1, blood cells were collected, and diluted 5-fold (by volume) with 1.0 volume % Triton X-100 solution, and then hemolyzed to prepare a hemolyzed sample. 150 μl of 1.0 mol/liter sodium iodoacetate solution (produced by Aldorich; hereinafter the same) was added to 50 μl of the hemolyzed sample and stirred, and then treated at 37° C. for 10 minutes. After the treatment, 400 μl of the FV solution was added to the sample, and then 1,400 μl of the redox solution A was added thereto so as to start a reaction. Then, the absorbance of the reaction solution was measured in the same way as in Example 1, and a relative value (%) to a control was determined. This measurement was determined as Comparative Example 2. Moreover, as the control, the same measurement as in the above was carried out except that distilled water was used in place of the hemolyzed sample.

In Comparative Example 3. measurement was carried out according to the same procedures as in Example 1 except that distilled water was used in place of the sodium iodoacetate solution. These results are shown in Table 2 below.

TABLE 2

|  | Relative value (%) |
|---|---|
| Comparative Example 2 | 37 |
| Comparative Example 3 | 35 |
| Control | 100 |

As shown in Table 2 above, it was confirmed that the influence of the reducing substance in the hemolyzed sample cannot be avoided with sodium iodoacetate, which has been conventionally used as an oxidizing agent.

Comparative Example 4

In this comparative example, a hemolyzed sample of erythrocytes was subjected to molecular weight fractionation, and then treated with sodium iodoacetate.

10 ml of blood from a healthy adult to which heparin was added was subjected to centrifugation (1630 G, for 10 minutes), and the plasma layer and leukocytes layer were removed with a pipette. To the erythrocytes layer obtained, physiological saline was added, and mixed slowly so that the erythrocytes are not hemolyzed. Then, it was subjected to centrifugation in the same way as in the above, and the supernatant was removed. This series of washing operations was repeated three times. Then, an equal amount (by volume) of distilled water was added to the erythrocytes obtained, so as to hemolyze the erythrocytes completely. Thereafter, it was subjected to centrifugation (4530 G, for 10 minutes) again, and membrane components were removed. The solution thus obtained was determined as Sample 1.

Next, Sample 1 was ultrafiltered by centrifugation (1630 G, for 4 hours) using CENTRIPREP 30 (produced by Millipore Corporation). A fraction of molecular weight of not less than 30,000 remained in the CENTRIPREP 30 was determined as Sample 2. The filtered solution was determined as Sample 3.

Next, Sample 3 was further ultrafiltered by centrifugation (1630 G, for 2 hours) using CENTRIPREP 10 (produced by Millipore Corporation). A fraction of molecular weight of not less than 10,000 but less than 30,000 remained in the CENTRIPREP 10 was determined as Sample 4. The filtered solution was determined as Sample 5.

Each of the above-mentioned samples was diluted with distilled water to prepare a diluted solution, and 400 μl of the FV solution was added to 200 μl of the diluted solution. Then, 1,400 μl of the redox reaction solution A was added thereto so as to start a reaction. Then, absorbance was measured in the same way as in Example 1, and a relative value (%) to a control was determined. Moreover, Samples 1 and 2 were diluted 80-fold, and Samples 3 to 5 were diluted 10-fold with distilled water. As a control, measurement was carried out in the same manner as in the above except that distilled water was used in place of the hemolyzed sample.

Furthermore, 150 μl of the sodium iodoacetate solution was added to 50 μl of the diluted solution of each sample and stirred, and thereafter treated at 37° C. for 10 minutes. Then, 400 μl of the FV solution was added to the treated sample, and thereafter 1,400 μl of the redox reaction solution A was added thereto so as to start a reaction. Absorbance was measured in the same way as in Example 1 above, and a relative value (%) to a control was determined. These results are shown in Table 3 below.

TABLE 3

|  | Relative value (%) |
|---|---|
| Sample 1 | 0 |
| Sample 2 | 7 |
| Sample 3 | 93 |
| Sample 4 | 100 |
| Sample 5 | 93 |
| Sample 1 + sodium iodoacetate | 0 |
| Sample 2 + sodium iodoacetate | 8 |
| Sample 3 + sodium iodoacetate | 98 |
| Sample 4 + sodium iodoacetate | 100 |
| Sample 5 + sodium iodoacetate | 98 |
| Control | 100 |

As shown in Table 3 above, the analytes in Sample 1 (not fractionated) and Sample 2 (the fraction of molecular weight of at least 30,000) were hardly measured. Also, these samples were hardly measured when treated with sodium iodoacetate. Accordingly, it was found that the influence of a reducing substance with a molecular weight of at least 10,000, particularly at least 30,000, was hardly avoided with sodium iodoacetate.

EXAMPLE 2

Comparative Example 5

In Example 2, a blood sample with treated with various types of tetrazolium compounds so as to eliminate the influence of amy reducing substance in the sample. The following shows the names and structures of the tetrazolium compounds used.

(1) Tetrazolium compounds having cyclic substituted groups with benzene rings at three positions of their tetrazole rings.

(1-1) WST-1

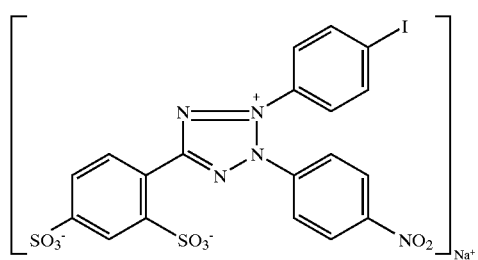

WST-1

2-(4-iodophenyl)-3-(4-nitrophenyl)-5-(2,4-disulfophenyl)-2H-tetrazolium, monosodium salt (1-2) WST-3

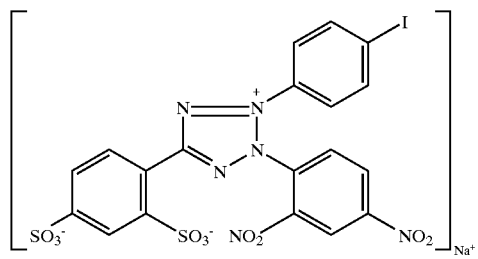

WST-3

2-(4-iodophenyl)-3-(2,4dinitrophenyl)-5-(2,4-disulfophenyl)-2H-tetrazolium, monosodium salt (1-3) WST-8

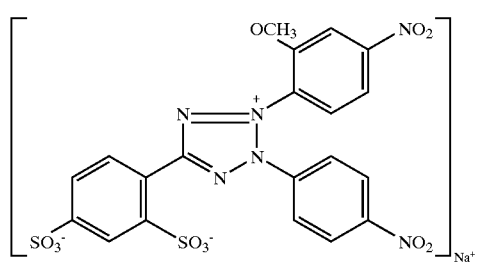

WST-8

2-(2-methoxy-4-nitrophenyl)-3-(4-nitrophenyl)-5-(2,4-disulfophenyl)-2H-tetrazolium, monosodium salt (1-4) INT

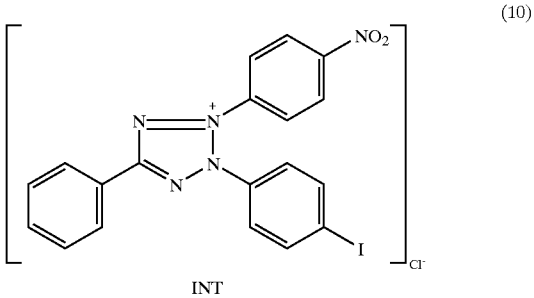

INT 2-(4-iodophenyl)-3-(4-nitrophenyl)-5-phenyl-2H-tetrazolium chloride (1-5) Neo-TB

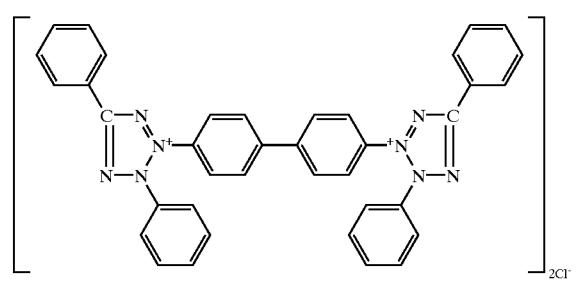

Neo-TB 3,3'-(1,1'-biphenyl-4,4'-diyl)-bis(2,5-diphenyl)-2H-tetrazolium chloride (1-6) NTB

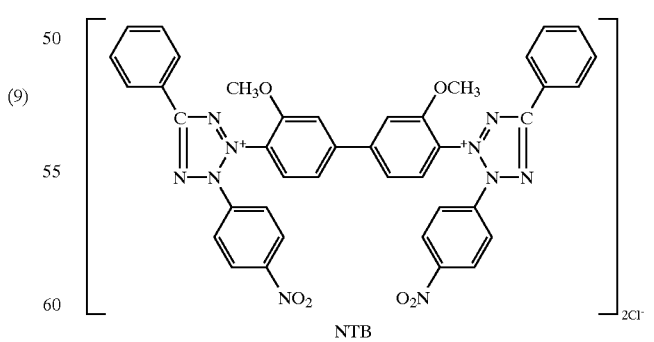

NTB 3,3'-[3,3'-dimethoxy-(1,1'-biphenyl)-4,4'-diyl]-bis[2-(4-nitrophenyl)-5-phenyl-2H-tetrazolium chloride]

(1-7) B329

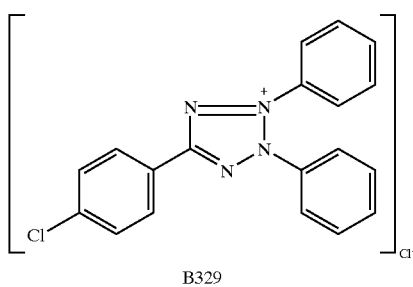

2,3-diphenyl-5-(4-chlorophenyl)tetrazolium chloride (1-8) D0883

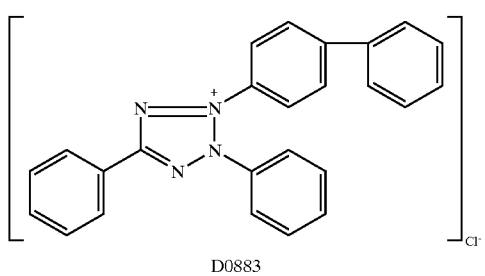

2,5-diphenyl-3-(p-diphenyl)tetrazolium chloride (1-9) D0884

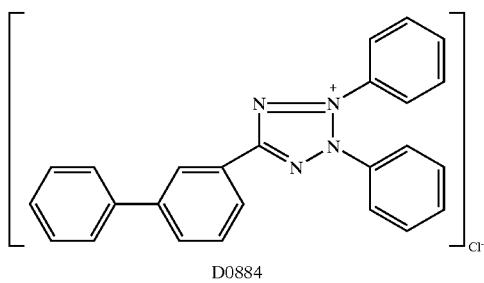

2,3-diphenyl-5-(p-diphenyl)tetrazolium chloride (1-10) D0915

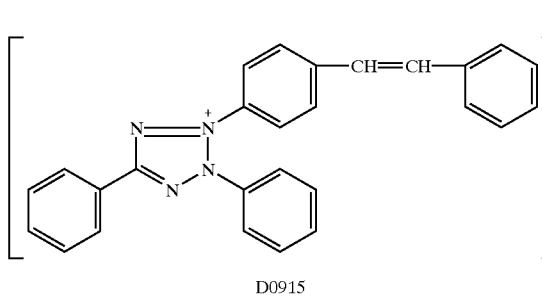

2,5-diphenyl-3-(4-styrylphenyl)tetrazolium chloride (1-11) T324

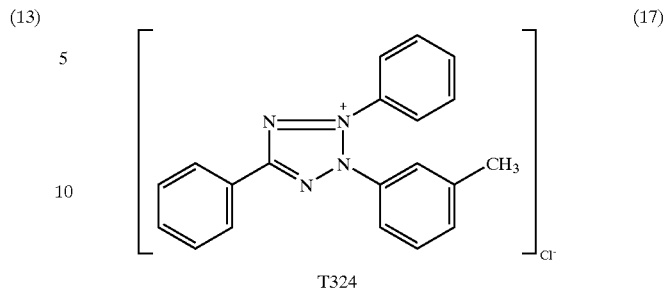

2,5-diphenyl-3-(m-tolyl)tetrazolium chloride (1-12) T326

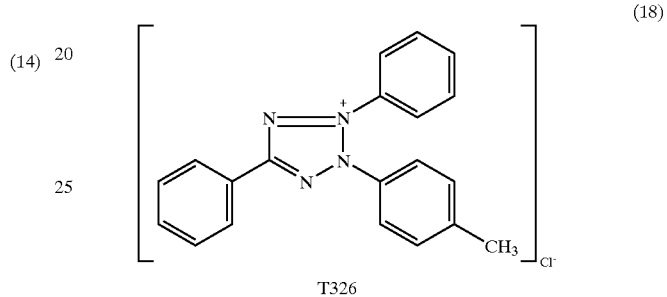

2,5-diphenyl-3-(p-tolyl)tetrazolium chloride (2) Tetrazolium compounds having cyclic substituted groups with benzene rings at two positions of their tetrazole rings and a cyclic substituted group other than having a benzene ring at one position thereof.

(2-1) B0325

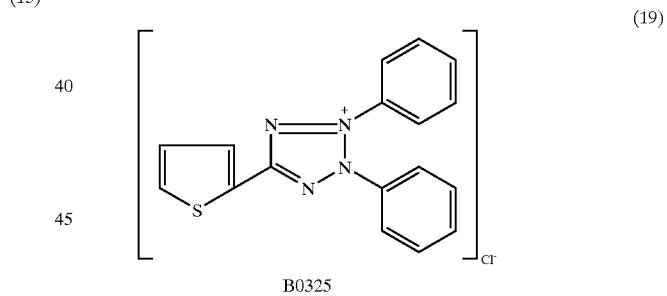

2,3-diphenyl-5-(2-thienyl)tetrazolium chloride (2-2) WST-4

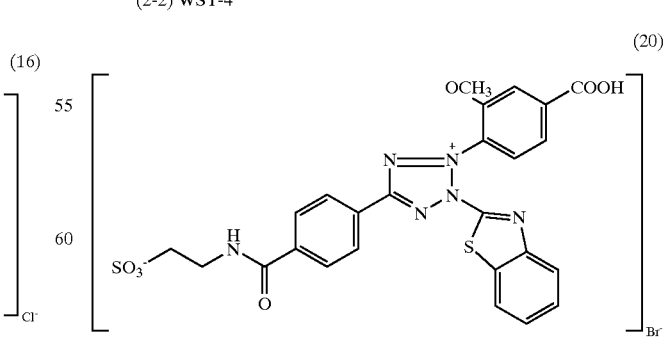

2-benzthiazoyl-3-(4-carboxy-2-methoxyphenyl)-5-[4-(2-sulfoethyl carbamoyl)phenyl]-2H-tetrazolium (2-3) WST-5

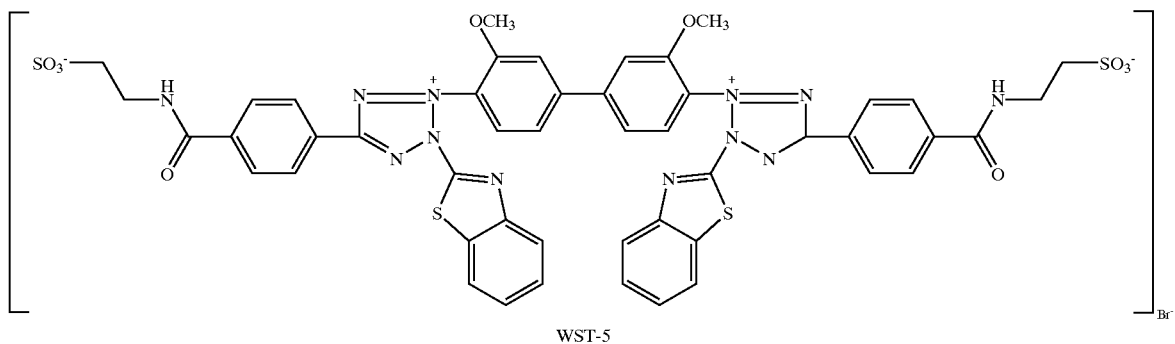

2,2'-dibenzthiazolyl-5,5'-bis[4-di(2-sulfoethyl)carbamoylphenyl]-3,3'-(3,3'-dimethoxy-4,4'-biphenylene)ditetrazolium, disodium salt (2-4) MTT

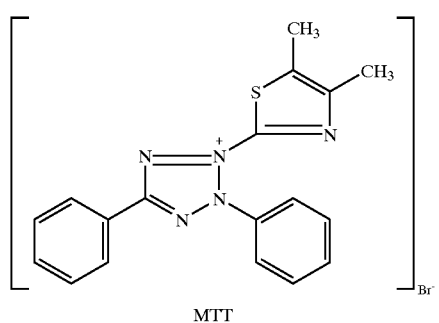

3-(4,5-dimethyl-2-thiazoyl)-2,5-diphenyl-2H-tetrazolium chloride (3) Tetrazolium compounds having cyclic substituted groups with benzene rings at two positions of their tetrazole rings and a non-cyclic substituted group at one position thereof.

(3-1) B0293

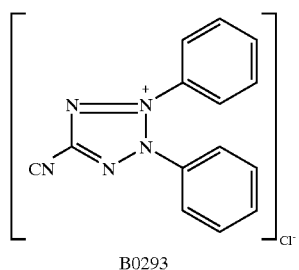

2,3-diphenyl-5-cyanotetrazolium chloride (3-2) B295

2,3-diphenyl-5-carboxytetrazolium chloride (3-3) B313

2,3-diphenyl-5-methyltetrazolium chloride (3-4) B319

2,3-diphenyl-5-ethyltetrazolium chloride

Moreover, WST-1, WST-3, WST-8, WST-4, WST-5, INT, MTT, NTB, and Neo-TB are products of DOJINDO LABORATORIES, and others are products of TOKYO KASEI KOGYO CO., LTD.

FV Solution

FV was added to 0.145 mol/liter KPB (pH 7.0) so that its concentration became 10 μmol/liter.

| Redox reaction solution B | |
|---|---|
| FAOD | 73 KU/liter |
| POD | 219 KU/liter |
| DA-64 | 146 μmol/liter |
| Distilled Water | remaining portion |

To 25 μl of 1.0 mol/liter CAPSO buffer (pH 10.0), 41.3 μl of the 10 volume % Triton X-100 solution and 1.65 μl of whole blood from a healthy adult were added, and it was quantified to 250 μl with distilled water. Then, it was further diluted 3-fold (by volume) with purified water so as to prepare a hemolyzed sample.

150 μl of each tetrazolium compound solution was added to 250 μl of the hemolyzed sample and stirred, and then treated at 37° C. for 60 minutes. Then, 55 μl of the FV solution was added to 25 μl of the sample, and thereafter 15 μl of the redox reaction solution B was added thereto so as to start a reaction. Then, absorbance was measured in the same way as in Example 1, and a relative value (%) to a control was determined. Moreover, the concentration of the tetrazolium compound solution was 0.5 mmol/liter for WST-5 and 5 mmol/liter for other solutions.

As the control, measurement was carried out in the same way as in the above except that distilled water was used in place of the hemolyzed sample. As Comparative Example 5, measurement was carried out according to the same procedures as in Example 2 except that distilled water was used in place of the tetrazolium compound solution. These results are shown in Table 4 below.

TABLE 4

| Tetrazolium compound | Relative value (%) |
|---|---|
| 1-1 | 90 |
| 1-2 | 94 |
| 1-3 | 89 |
| 1-4 | 90 |
| 1-5 | 88 |
| 1-6 | 94 |
| 1-7 | 94 |
| 1-8 | 91 |
| 1-9 | 93 |
| 1-10 | 91 |
| 1-11 | 91 |
| 1-12 | 74 |
| 2-1 | 81 |
| 2-2 | 42 |
| 2-3 | 44 |
| 2-4 | 47 |
| 3-1 | 76 |
| 3-2 | 74 |
| 3-3 | 74 |
| 3-4 | 68 |
| Comparative Example 5 | 35 |
| Control | 100 |

As shown in Table 4 above, reliability of the measured values was improved by treating the hemolyzed sample with each tetrazolium compound, particularly when the tetrazolium compounds (1-1) to (1-12) having cyclic substituted groups with benzene rings at three positions of their tetrazole rings were used.

EXAMPLE 3

In Example 3, WST-3, WST-1, WST-8, and INT were used as the tetrazolium compound so as to vary the pH during the treatment. The following shows buffers used in this example.

Buffer Solutions 1.0 mol/liter CHES buffer (pH 9.0)
1.0 mol/liter CAPSO buffer (pH 10.0)
1.0 mol/liter CAPS buffer (pH 11.0)

Except that each of the above different buffers were used, treatment was performed using each of the above-mentioned tetrazolium compounds according to the same procedures as in Example 2, and absorbance was measured. Moreover, relative values were determined by setting the absorbance of WST-3 at pH 10.0 as 100%. The results showed that the relative values were 100% when each of the above-mentioned buffers (pH 9, 10, 11) was used for each tetrazolium compound, and no influence by the pH was observed.

EXAMPLE 4

Comparative Example 6

In Example 4, treatment was carried out using WST-3 while setting the final diluting factor of a whole blood sample in the reaction solution to about 100-fold.

Except that 33 μl of whole blood obtained from a healthy adult and 50 μl of 1.0 mol/liter CAPSO buffer (pH 10) were used, hemolysis was carried out in the same manner as in Example 2. The sample was quantified to 250 μl by adding 125.7 μl of distilled water. Then, it was diluted 3-fold (by volume) with purified water so as to prepare a hemolyzed sample.

15 μl of 5 mmol/liter WST-3 solution was added to 25 μl of the hemolyzed sample and stirred, and then treated at 37° C. for 5 minutes. Then, 55 μl of 6 μmol/liter FV solution was added to the sample. Thereafter, 15 μl of the redox reaction solution B was added thereto so as to start a reaction. Then, absorbance was measured in the same way as in Example 1, and a relative value (%) to a control was determined. As the control, measurement was carried out in the same manner as the above except that distilled water was used in place of the hemolyzed sample. As Comparative Example 6, measurement was performed in the same way as the above except that distilled water was used in place of the WST-3 solution. These results are shown in Table 5 below.

TABLE 5

| | Relative value (%) |
|---|---|
| Example 4 | 80 |
| Comparative Example 6 | 0 |
| Control | 100 |

In Example 4, even when the concentration of the reducing substance in the reaction solution was increased by lowering the final diluting factor of the whole blood sample, the influence of the reducing substance was eliminated as indicated in Table 5, and the measured values obtained had excellent reliability. On the other hand, in Comparative Example 6 in which the sample was not treated with WST-3, a slight color was developed immediately after the start of the reaction, but shortly thereafter the color was degraded, and it was completely faded after 5 minutes. Therefore, absorbance could not be measured, so that the relative value was 0% as shown in Table 5 above.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A method of measuring an analyte in a sample using a redox reaction, comprising:

eliminating the influence of any reducing substance contained in the sample prior to conducting the redox reaction, the influence of any reducing substance being eliminated by adding a tetrazolium compound prior to the redox reaction;

forming a reducing substance or an oxidizing substance derived from the analyte;

measuring the quantity of the formed substance derived from the analyte by the redox reaction; and determining the quantity of the analyte from the quantity of the formed substance derived from the analyte.

2. The method according to claim 1, wherein the tetrazolium compound has cyclic substituted groups in at least two positions of its tetrazole ring.

3. The method according to claim 2, wherein at least two of the cyclic substituted groups have benzene rings.

4. The method according to claim 1, wherein the tetrazolium compound has cyclic substituted groups in at least three positions of its tetrazole ring, and at least two of the cyclic substituted groups have benzene rings.

5. The method according to claim 2, wherein at least one of the cyclic substituted groups has an electron attractive functional group.

6. The method according to claim 5, wherein the electron attractive functional a group is at least one functional group selected from the group consisting of halogen atoms and ether, ester, carboxyl, acyl, nitroso, nitro, hydroxyl, and sulfo groups.

7. The method according to claim 1, wherein the tetrazolium compound has benzene rings at positions 2 and 3 of its tetrazole ring, and at least one of the benzene rings has at least one functional group selected from the group consisting of halogen atoms and carboxyl, nitro, hydroxyl, sulfo, methoxy, and ethoxy groups.

8. The method according to claim 1, wherein the tetrazolium compound is added so that its concentration falls in a range of 0.001 to 100 $\mu$mol per 1 $\mu$l of the sample.

9. The method according to claim 1, wherein the sample is whole blood, and the tetrazolium compound is added so that its concentration falls in a range of 0.001 to 10 $\mu$mol per 1 $\mu$l of the whole blood.

10. The method according to claim 1, wherein the oxidizing substance derived from the analyte is hydrogen peroxide, and the quantity of the hydrogen peroxide is measured by the redox reaction.

11. The method according to claim 10, wherein the quantity of the hydrogen peroxide is measured using a peroxidase and a substrate that develops color by oxdiation.

12. The method of claim 1, wherein the analyte is a component in erythrocytes.

13. The method according to claim 10, wherein the analyze is a glycated protein in erythrocytes, and the hydrogen peroxide is formed by decomposing a sugar portion of the glycated protein by oxidation with fructosyl amino acid oxidase.

14. The method according to claim 1, wherein a molecular weight of the reducing substance in the sample is at least 10,000.

15. The method according to claim 1, wherein the reducing substance in the sample is a protein.

16. The method according to claim 1, wherein the reducing substance in the sample is hemoglobin.

* * * * *

UNITED STATES PATENT AND TRADEMARK OFFICE
CERTIFICATE OF CORRECTION

PATENT NO. : 6,514,720 B2 Page 1 of 1
DATED : February 4, 2003
INVENTOR(S) : Komori et al.

It is certified that error appears in the above-identified patent and that said Letters Patent is hereby corrected as shown below:

<u>Title page,</u>
Insert the following:
-- [30]    Foreign Application Priority Data
   Nov. 17, 1998   (JP)……………………………..10-343583 --

Signed and Sealed this

Twentieth Day of January, 2004

JON W. DUDAS
*Acting Director of the United States Patent and Trademark Office*